United States Patent [19]

Hirabayashi et al.

[11] Patent Number: 4,543,309

[45] Date of Patent: Sep. 24, 1985

[54] HEAT-DEVELOPABLE IMAGE-PATTERN RECORDING MATERIAL

[75] Inventors: Shigeto Hirabayashi, Hachioji; Toyoaki Masukawa, Hinode; Wataru Ishikawa, Hachioji; Tetsuya Harada, Chofu, all of Japan

[73] Assignee: Konishiroku Photo Industry Co., Ltd., Tokyo, Japan

[21] Appl. No.: 610,864

[22] Filed: May 16, 1984

Related U.S. Application Data

[63] Continuation of Ser. No. 491,389, May 4, 1983, abandoned.

[30] Foreign Application Priority Data

May 7, 1982 [JP] Japan .................................. 57-76836

[51] Int. Cl.$^4$ .................... G03G 13/00; G03G 13/22; G03C 1/02
[52] U.S. Cl. ......................................... 430/31; 430/52; 430/611; 430/619; 430/618; 346/135.1; 204/2; 204/18.1
[58] Field of Search ............... 430/611, 618, 619, 620, 430/603, 564, 353, 52, 31; 252/518, 501.1; 346/135.1; 204/2, 18.1

[56] References Cited

U.S. PATENT DOCUMENTS

| | | | |
|---|---|---|---|
| 3,330,663 | 7/1967 | Weyde et al. | 430/620 |
| 4,188,212 | 2/1980 | Fujiwara et al. | 252/518 |
| 4,234,670 | 11/1980 | Kaukeinen et al. | 430/619 |
| 4,409,307 | 10/1983 | Lelental et al. | 430/52 |

OTHER PUBLICATIONS

Research Disclosure 16979 (Tan, et al), vol. No. 169, May 1978.
Research Disclosure 17029 (Carpenter, et al), vol. No. 170, Jun. 1978.

Primary Examiner—Won H. Louie
Attorney, Agent, or Firm—Finnegan, Henderson, Farabow, Garrett & Dunner

[57] ABSTRACT

A composition suitable for application as a layer on a heat-developable image-pattern recording material to enhance the developability and stability thereof, comprising a silver salt of a benzotriazole, a reducing agent, a binder, at least one compound having the following Formula [I]:

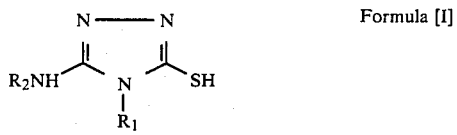

Formula [I]

wherein $R_1$ represents a hydrogen, an amino radical, or a substituted or unsubstituted alkyl, alkenyl or aryl radical; $R_2$ represents a hydrogen, an amino alkyl, alkenyl or aryl radical is disclosed. The disclosed composition has improved developability.

8 Claims, No Drawings

HEAT-DEVELOPABLE IMAGE-PATTERN RECORDING MATERIAL

This is a continuation of application Ser. No. 491,389, filed May 4, 1983, abandoned.

BACKGROUND OF THE INVENTION

1. Field of the Invention

The present invention relates to a heat-developable image-pattern recording material and, more particularly, to a heat-developable image-pattern recording material remarkably improved in the developability thereof.

Herein, the heat-developable image-pattern recording materials mean recording materials in which a latent image-pattern formed by some process is amplified by a heat-development and an image-pattern is thus obtained, and more concretely, such heat-developable image-pattern recording materials are classified into two kinds according to the latent image-pattern forming methods, one is a heat-developable light-sensitive material, wherein a latent image-pattern is formed by making use of a silver halide and by applying light thereto, and another one is an electro thermo-recording material, wherein a latent image-pattern is formed by applying an electric charge thereto.

2. Description of the Prior Art

With reference to heat-developable light-sensitive materials, there are descriptions in, for example, Japanese patent examined publication Nos. 4921/1968 and 4924/1968, and the like, wherein the light-sensitive materials comprising an organic silver salt, silver halide and reducing agent are disclosed. These heat-developable light-sensitive materials are to obtain silver image-patterns in the so-called dry physical development process that a latent image-pattern is formed on silver halide by exposing to light, and making the latent image-pattern serve as the catalytic nuclei, an oxidation-reduction reaction is performed with an organic silver salt and a reducing agent when the light-sensitive material is heated.

With reference to electro thermo-recording materials, there are descriptions in, for example, Japanese Patent Publication Open to Public Inspection (hereinafter referred to as Japanese Patent O.P.I. Publication) Nos. 63621/1976, 23635/1978, 133041/1978, 144753/1978, 101333/1979 and 106229/1979, and the like, wherein the electro thermo-image-pattern recording materials comprising an organic silver salt and a reducing agent are disclosed.

In general, image-pattern forming compositions to be used in the abovementioned heat-developable image-pattern materials fundamentally comprise an organic silver salt and a reducing agent, and in addition thereto, a development accelerator and a color toning agent may be added thereto with the purposes of making developments accelerate to obtain an image-pattern having a relatively higher maximum density and an excellent tone, that has been well known.

As for the development accelerators and the color toning agents, there are described in, for example, Japanese Patent O.P.I. Publication Nos. 4928/1971, 6077/1971, 5019/1974, 5020/1974, 91215/1974, 107727/1974, 2524/1975, 67132/1975, 67641/1974, 114217/1975, 33722/1977, 99813/1977, 1020/1978, 55115/1978, 76020/1978, 125014/1978, 156523/1979, 156524/1979, 15625/1979, 156526/1979, 4060/1980, 4061/1980, and 32015/1980; W. German Pat. Nos. 2,140,406, 2,147,063, and 2,220,618; and U.S. Pat. Nos. 3,080,254, 3,847,612, 3,782,941, 3,994,732, 4,123,282 and 4,201,582; and the like; wherein the following compounds are given as the examples thereof: derivatives each of a phthalimide, pyrazolone, quinazolinone, N-hydroxynaphthalimide, benzoxadine, naphthoxadinedione, 2,3-dihydrophthaladinedione, 2,3-dihydro-1,3-oxadine-2,4-dione, oxypyridine, aminopyridine, hydroxyquinoline, aminoquinoline, isocarbostyryl, sulfonamide, 2H-1,3-benzothiazine-2,4-(3H)dione, benzotriazine, mercaptotriazole, dimercaptotetrazapentalene, phthalic acid, phtalazine, naphthalic acid, phthalamic acid, phthaladinone, and the like. Some of these compounds mostly increase fog at the same time when a development is effectively accelerated, though, and some of them mostly deteriorate the preservation stability of a heat-developable image-pattern recording material, before and after the development thereof is processed. Therefore, the compounds having a satisfactory performance has not yet obtained.

OBJECTS OF THE INVENTION

Accordingly, it is an object of the invention to provide a heat-developable image-pattern recording material having an excellent developability, high maximum density and only a little fog.

Another object of the invention is to provide a heat-developable image-pattern recording material having an excellent preservation stability before and after the development thereof is processed.

SUMMARY OF THE INVENTION

The invention comprises a heat-developable image-pattern recording material having on a support a heat-developable image-pattern recording layer containing
(a) a silver salt of a benzotriazole,
(b) a reducing agent,
(c) a binder and
(d) at least one of a compound having the following Formula [I]:

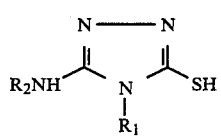

Formula [I]

wherein
R$_1$ represents a hydrogen, an amino radical, substituted or unsubstituted alkyl, alkenyl or aryl radical;
R$_2$ represents a hydrogen, an amino, alkyl, alkenyl or aryl radical.

DETAILED DESCRIPTION OF THE INVENTION

The following is the detailed description of the heat-developable image-pattern recording materials of the invention:

As for the concrete examples of (a) silver salts of a benzotriazole (hereinafter collectively referred to as benzotriazole silver), the following compounds may be given: e.g.; benzotriazole silver, 5-chlorobenzotriazole silver, 5-methylbenzotriazole silver, 5-aminobenzotriazole silver, 5-methoxybenzotriazole silver, 4-nitrobenzotriazole silver, 5-nitrobenzotriazole silver, 5-nitro-6-chlorobenzotriazole silver, 5-nitro-6-methylbenzotriazole silver, 5-nitro-6-methoxybenzotriazole silver, 5-nitro-7-phenylbenzotriazole silver, 4-hydroxy-5-nitrobenzotriazole silver, 4-hydroxy-7-nitrobenzotriazole silver, 4-hydroxy-5,7-dinitrobenzotriazole silver, 4-hydroxy-5-nitro-6-chlorobenzotriazole silver, 4-hydroxy-5-nitro-6-methylbenzotriazole silver, 4-sulfo-6-nitrobenzotriazole silver, 4-carboxy-6-nitrobenzotriazole silver, 5-carboxy-6-nitrobenzotriazole silver, 4-carbamoyl-6-nitrobenzotriazole silver, 4-sulfamoyl-6-nitrobenzotriazole silver, 5-carboxymethyl-6-nitrobenzotriazole silver, 5-hydroxycarbonylmethoxy-6-nitrobenzotriazole silver, 5-nitro-7-cyanobenzotriazole silver, 5-amino-6-nitrobenzotriazole silver, 5-nitro-7-(P-nitrophenyl)benzotriazole silver, 5,7-dinitro-6-methylbenzotriazole silver, 5,7-dinitro-6-chlorobenzotriazole silver, 5,7-dinitro-6-methoxybenzotriazole silver, 4-hydroxybenzotriazole silver, 5-hydroxybenzotriazole silver, 4-sulfobenzotriazole silver, 5-sulfobenzotriazole silver, benzotriazole silver-4-sodium sulfonate, benzotriazole silver-5-sodium sulfonate, benzotriazole silver-4-potassium sulfonate, benzotriazole silver-5-potassium sulfonate, benzotriazole silver-4-ammonium sulfonate, benzotriazole silver-5-ammonium sulfonate, 4-carboxybenzotriazole silver, 5-carboxybenzotriazole silver, benzotriazole silver-4-sodium carbonate, benzotriazole silver-5-sodium carbonate, benzotriazole silver-4-potassium carbonate, benzotriazole silver-5-potassium carbonate, benzotriazole silver-4-ammonium carbonate, benzotriazole silver-5-ammonium carbonate, 5-carbamoyl benzotriazole silver, 4-sulfamoyl benzotriazole silver, 5-carboxy-6-hydroxybenzotriazole silver, 5-carboxy-7-sulfobenzotriazole silver, 4-hydroxy-5-sulfobenzotriazole silver, 4-hydroxy-7-sulfobenzotriazole silver, 5,6-dicarboxybenzotriazole silver, 4,6-dihydroxybenzotriazole silver, 4-hydroxy-5-chlorobenzotriazole silver, 4-hydroxy-5-methylbenzotriazole silver, 4-hydroxy-5-methoxybenzotriazole silver, 4-hydroxy-5-nitrobenzotriazole silver, 4-hydroxy-5-cyanobenzotriazole silver, 4-hydroxy-5-aminobenzotriazole silver, 4-hydroxy-5-acetoamido benzotriazole silver, 4-hydroxy-5-benzenesulfonamide benzotriazole silver, 4-hydroxy-5-hydroxycarbonylmethoxy benzotriazole silver, 4-hydroxy-5-ethoxycarbonylmethoxy benzotriazole silver, 4-hydroxy-5-carboxymethyl benzotriazole silver, 4-hydroxy-5-ethoxycarbonylmethyl benzotriazole silver, 4-hydroxy-5-phenylbenzotriazole silver, 4-hydroxy-5-(P-nitrophenyl)benzotriazole silver, 4-hydroxy-5-(P-sulfophenyl)benzotriazole silver, 4-sulfo-5-chlorobenzotriazole silver, 4-sulfo-5-methylbenzotriazole silver, 4-sulfo-5-methoxybenzotriazole silver, 4-sulfo-5-cyanobenzotriazole silver, 4-sulfo-5-aminobenzotrizole silver, 4-sulfo-5-acetoamidobenzotriazole silver, 4-sulfo-5-benzenesulfonamide benzotriazole silver, 4-sulfo-5-hydroxycarbonylmethoxy benzotriazole silver, 4-sulfo-5-ethoxycarbonylmethoxy benzotriazole silver, 4-hydroxy-5-carboxybenzotriazole silver, 4-sulfo-5-carboxymethyl benzotriazole silver, 4-sulfo-5-ethoxycarbonylmethyl benzotriazole silver, 4-sulfo-5-phenylbenzotriazole silver, 4-sulfo-5-(P-nitrophenyl)benzotriazole silver, 4-sulfo-5-(P-sulfophenyl)benzotriazole silver, 4-sulfo-5-methoxy-6-chlorobenzotriazole silver, 4-sulfo-5-chlor-6-carboxy benzotriazole silver, 4-carboxy-5-chlorobenzotriazole silver, 4-carboxy-5-methylbenzotriazole silver, 4-carboxy-5-nitrobenzotriazole silver, 4-carboxy-5-aminobenzotriazole silver, 4-carboxy-5-methoxybenzotriazole silver, 4-carboxy-5-acetamidebenzotriazole silver, 4-carboxy-5-ethoxycarbonylmethoxy benzotriazole silver, 4-carboxy-5-carboxymethyl benzotriazole silver, 4-carboxy-5-phenyl benzotriazole silver, 4-carboxy-5-(P-nitrophenyl)benzotriazole silver, 4-carboxy-5-methyl-7-sulfobenzotriazole silver, and the like. These compounds may be allowed to use independently or in combination of two or more kinds thereof.

Heat-developable image-pattern recording layer of the heat developable image-pattern recording materials of the invention may be allowed to provide as a single layer or as a multiple layer. The abovementioned benzotriazole silver is used in every layer in the proportion of 0.5–50 mg of silver converted per 1 $dm^2$ and, more preferably, 1–20 mg/$dm^2$ in every layer.

In the case of providing the abovementioned multiple layer, it is possible to adjust the tones of an image-pattern or, the toe, shoulder or whole curve of an image-pattern density characteristics curve by changing the kinds or contents of such materials as the abovementioned benzotriazole silver and the undermentioned reducing agents which are to be contained in one and the same layer. Besides the above, it is also possible to increase the stability of the abovementioned recording materials by dividing into a layer containing a benzotriazole silver and another layer containing a reducing agent, respectively. In this case, it is preferred that the compounds of the invention having the formula [I] are to be contained in a layer containing a benzotriazole silver.

Further, as for (b) the reducing agents to be used in the invention, the examples thereof may be given as follows: a phenol such as P-phenylphenol, P-methoxyphenol, 2,6-di-tert-butyl-P-cresol, N-methyl-P-aminophenol, and the like; a sulfoamidophenol such as 4-benzenesulfonamidophenol, 2-benzenesulfonamidophenol, 2,6-dichloro-4-benzenesulfonamidophenol, 2,6-dibromo-4-(P-toluenesulfonamido)phenol, and the like; a di- or polyhydroxybenzene such as hydroquinone, tert-butylhydroquinone, 2,6-dimethylhydroquinone, chlorohydroquinone, carboxyhydroquinone, catechol, 3-carboxycatechol and the like; a naphthol such as α-naphthol, β-naphthol, 4-aminonaphthol, 4-methoxynaphthol and the like; a hydroxybinaphthyl and a methylenebisnaphthol such as 1,1'-dihydroxy-2,2'-binaphthyl, 6,6'-dibromo-2,2'-dihydroxy-1,1'-binaphthyl, 6,6'-dinitro-2,2'-dihydroxy-1,1'-binaphthyl, 4,4'-dimethoxy-1,1'-dihydroxy-2,2'-binaphthyl; bis(2-hydroxy-1-naphthyl)methane and the like; a methylenebisphenol such as 1,1-bis(2-hydroxy-3,5-dimethylphenyl)-3,5,5-trimethylhexane, 1,1-bis(2-hydroxy-3-tert-butyl-5-methylphenyl)methane, 1,1-bis(2-hydroxy-3,5-di-tert-butylphenyl)methane, 2,6-methylenebis(2-hydroxy-3-tert-butyl-5-methylphenyl)-4-methylphenol, α-phenyl-α,α-bis(2-hydroxy-3,5-di-tert-butylphenyl)methane, α-phenyl-60 ,α-bis(2-hydroxy-3-tert-butyl-5-methylphenyl)methane, 1,1-bis(2-hydroxy-3,5-dimethylphenyl)-2-methylpropane, 1,1,5,5-tetrakis(2-hydroxy-3,5-dimethylphenyl)-2,4-ethylpentane, 2,2-bis(4-hydroxy-3,5-dimethylphenyl)propane, 2,2-bis(4-hydroxy-3-methyl-5-tert-butylphenyl)propane, 2,2-bis(4-hydroxy-3,5-di-tert-butylphenyl)propane and the like; an ascorbic acid; a 3-pyrazolidone; a pyrazoline; a pyrazolone; a hydrazone; and aparaphenylenediamine.

And, in the case of using a hydrazone and a paraphenylenediamine to serve as a reducing agent, a color image-pattern may be obtained by making combination use thereof with a compound having such an active methylene as pyrazolone, pyrazolotriazole, indazole, pyrazoloimidazole, pyrazoline and the like, and a phenol compound and a naphthol compound as described in U.S. Pat. Nos. 3,531,286, and 3,764,328, and Japanese Patent O.P.I. Publication No. 27132/1981.

The abovementioned reducing agent may be used independently or in combination. The amount of the reducing agent to be used depends upon the kinds of benzotriazole silvers and other additives and is normally from 0.05 to 10 moles per mole of an organic benzotriazole silver and, more preferably, from 0.1 to 3 moles.

The image-pattern recording materials of the invention are allowed to contain a light-sensitive silver halide, if needed. As for the light-sensitive silver halide, there may be given the examples such as silver chloride, silver bromide, silver iodide, silver chlorobromide, silver chloroiodide, silver iodobromide, silver chlorobromoiodide and the like. These light-sensitive silver halide may be prepared in any arbitrary processes such as a single- or double-jet process which has been publicly known in the fields of photographic technique. Particularly, in the invention, a favorable result may be obtained from the light-sensitive silver halide emulsions prepared in accordance with the ordinary technique for preparing a silver halide gelatin emulsion.

These light-sensitive silver halide emulsions may also be allowed to chemically sensitize in an arbitrary process having been publicly-known in the field of photographic technique. The sensitization processes include various ones such as a gold sensitization, sulphur sensitization, gold-sulphur sensitization, reduction sensitization and the like. Silver halide of the abovementioned light-sensitive emulsion may be of coarse particle or fine particle, either. Inter alia, the preferred particle size is approximately 1.5 microns to 0.001 micron in diameter and, more preferably, from approx. 0.5 to 0.05 microns.

Light-sensitive silver halide emulsion thus prepared may be applied to a heat-developable image-pattern recording layer which is a component layer of an image-pattern recording material relating to the invention.

In the other types of the processes for preparing a light-sensitive silver halide, there may be included the process wherein a component for forming a light-sensitive silver salt is co-existed with a benzotriazole silver and a light-sensitive silver halide is formed in a part of the benzotriazole silver. As for the components for forming a light-sensitive silver salt to be used in this preparation process, there are given the following examples:

an organic halogenide, such as a halogenide represented by MXn, wherein M is hydrogen, $NH_4$ radical or a metal atom, X is Cl, Br or I, and when M is hydrogen or $NH_4$ radical, n is 1 and when M is a metal atom, n is the same number as the valence of the metal. As for the atoms of the metals there are the examples given as follows: Atom of lithium, sodium, potassium, rubidium, caesium, copper, gold, beryllium, magnesium, calcium, strontium, barium, zinc, cadmium, mercury, aluminium, indium, lanthanum, ruthenium, thallium, germanium, tin, lead, antimony, bismuth, chrome, molybdenum, tungsten, manganese, rhenium, iron, cobalt, nickel, rhodium, palladium, osmium, iridium, platinum, cerium and the like;

a halogen-containing metal complex, such as $K_2PtCl_6$, $K_2PtBr_6$, $HAuCl_4$, $(NH_4)_2IrCl_6$, $(NH_4)_3IrCl_6$, $(NH_4)_2RuCl_6$, $(NH_4)_3RuCl_6$, $(NH_4)_3RhCl_6$, $(NH_4)_3RhBr_6$ and the like;

an onium halide, such as a quaternary ammonium halide, e.g., tetramethyl ammonium bromide, trimethylphenyl ammonium bromide, cetylethyldimethyl ammonium bromide, 3-methylthiazolium bromide, and trimethylbenzyl ammonium bromide; a quaternary phosphonium halide, e.g., tetraethylphosphonium bromide; a tertiary sulfonium halide, e.g., benzylethylmethyl bromide and 1-ethylthiazolium bromide;

a halogenated hydrocarbon, such as iodoform, bromoform, carbon tetrabromide, 2-bromo-2-methyl propane and the like;

an N-halogenate, such as N-chlorosuccinimide, N-bromosuccinimide, N-bromophthalimide, N-bromoacetamide, N-iodosuccinimide, N-bromophthalazinone, N-chlorophthalazinone, N-bromoacetanilide, N,N-dibromobenzenesulfonamide, N-bromo-N-methylbenzenesulfonamide, 1,3-dibromo-4,4-dimethylhydantoin and the like; and besides, other halogen-containing compounds, such as triphenylmethyl chloride, triphenylmethyl bromide, 2-bromobutyric acid, 2-bromethanol and the like.

These light-sensitive silver halide and the components for forming light-sensitive silver salts may be combinedly used in various processes. The amount used thereof is 0.001 to 1.0 mole to one mole of a benzotriazole silver and, more preferably, 0.01 to 0.3 moles.

Binders (c) to be used in the invention may be of hydrophobic or hydrophilic material, either, and may also be of transparent or translucent, either. There are given the concrete examples thereof as follows: a variety of synthetic or natural macromolecular materials such as polyvinyl butyral, polyvinyl acetate, ethyl cellulose, polymethyl methacrylate, cellulose acetate, cellulose acetate butylate, polyvinyl alcohol, gelatin, gelatin derivatives and the like.

With reference to 3-amino-5-mercapto-1,2,4-triazole derivatives which are the compounds each having the aforegiven formula [I] and displaying the remarkable features in the invention.

In Formula [I], an alkyl radical represented by $R_1$ is of the normal chain type, the branched chain type or the cyclic type, and is preferably an alkyl radical having one to 12 carbon atoms. These alkyl radicals may also be substituted. The examples of the substituents are hydroxy radicals, phenyl radicals which may be substituted by halogen atoms, and the like. The examples of the alkyl radicals are given as radicals of a methyl, dichloromethyl, trifluoromethyl, ethyl, propyl, 3-hydroxypropyl, butyl, isobutyl, tertbutyl, pentyl, isopentyl, hexyl, heptyl, octyl, decyl, dodecyl, cyclohexyl, or the like.

An alkenyl radical represented by $R_1$ is preferably of the normal chain type and has 1 to 5 carbon atoms and may also be substituted. The examples of the substituents are a halogen or a hydroxy radical. Such alkenyl radicals are those of a vinyl, 1-propenyl, 2-propenyl, 1,3-butadienyl, 2-pentenyl, 3-hydroxy-1-propenyl, 2-chloro-2-propenyl and the like, for example.

Further, an aryl radical represented by $R_1$ are preferably of 6 carbon atoms, and may be substituted. The substituents are, for example, an amino radical, methoxy radical, a halogen and the like. The aryl radicals are, for example, those of a phenyl, p-aminophenyl, p-methoxyphenyl, m-carboxyphenyl, m-chlorophenyl, p-nitrophenyl and the like.

Also, in Formula [I], an alkyl, alkenyl and aryl radicals represented by $R_2$ are the same alkyl, alkenyl and aryl radicals respectively not having the abovementioned substituents being represented by $R_1$.

As for the concrete examples of the compounds having the Formula [I], the following compounds may be exemplified, however, the compounds of the invention shall not be limited thereto.

[Exemplified Compounds]

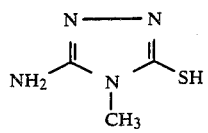
1.

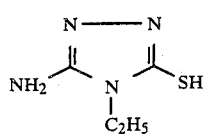
2.

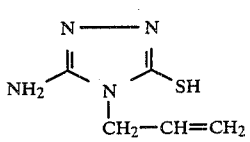
3.

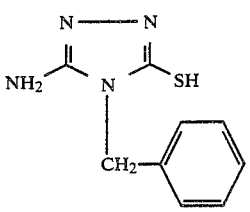
4.

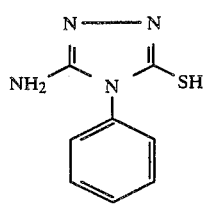
5.

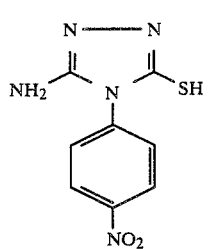
6.

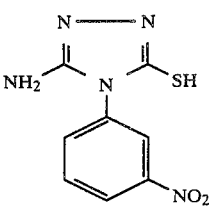
7.

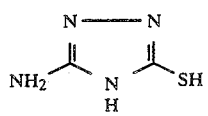
8.

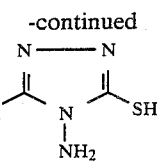
9.

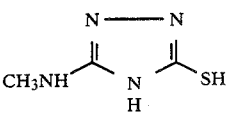
10.

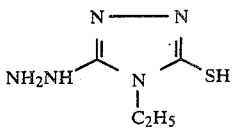
11.

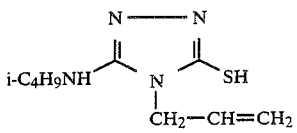
12.

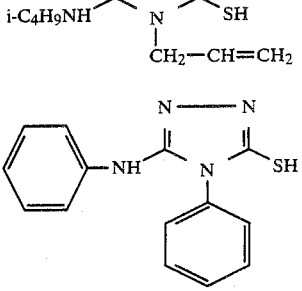
13.

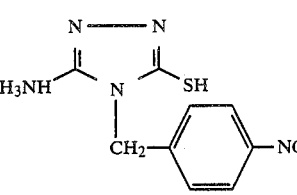
14.

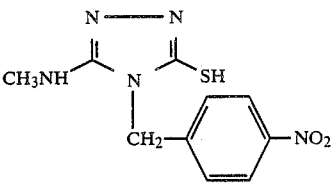
15.

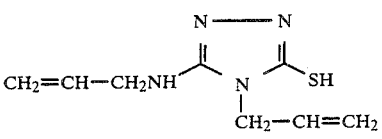

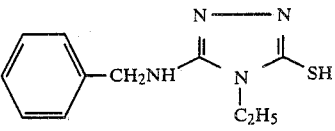
17.

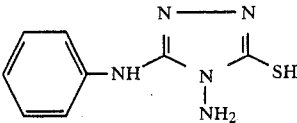

The following is the description on how to synthesize the compounds of the invention, and further, the other compounds may also be synthesized in a similar process.

Synthesis Example-1 (Compound No. 2)

Ethyl isocyanate of 80 g were dissolved in 100 ml of dimethyl formaldehyde, and 90 g of aminoguanidine sulfate were added to the solution, and then the heating and agitation were applied to the solution up to 100° C. for 4 hours time, respectively. Then, 300 ml of aqueous solution of 3N-NaOH were added to thus obtained reacted solution and the heat-reflux was made for one hour. After the reacted solution was cooled, the reacted solution was neutralized with concentrated hydrochloric acid and 400 ml of water were further added thereto, and when the solution was cooled, crystals were precipitated therefrom. The crystals were filtrated and recrystallized with 600 ml of water, and thus, Compound No. 2 was prepared. (Melting point: 195°-198° C.)

Synthesis Example-2 (Compound No. 4)

Benzyl isocyanate of 150 g were dissolved in 200 ml of ethanol, 160 g of aminoguanidine sulfate were added, and then, heat-reflux was made for 20 hours to obtain a reacted solution.

Ethanol was distilled off from the reacted solution under reduced pressure and 600 ml of aqueous 3N-NaOH solution were added to the residue, and then heat-reflux was applied thereto for two hours. After cooling, the reacted solution was neutralized with concentrated hydrochloric acid. When cooled the neutralized solution, crystals were precipitated therefrom. The crystals were then filtrated and recrystallized with 1000 ml of water, and thus Compound No. 4 was prepared. (Melting point: 206°-208° C.)

Synethsis Example-3 (Compound No. 5)

Phenyl isocyanate of 135 g were dissolved in 150 ml of dimethyl formamide, and 110 g of aminoguanidine hydrochloride were added to the solution, and then the heating and agitation were applied to the solution up to 100° C. and for 4 hours time, respectively. Then, 600 ml of aqueous solution of 2N-NaOH were added to thus obtained reacted solution and the heat-reflux was made for 3 hours. After the reacted solution was cooled, the reacted solution was neutralized with concentrated hydrochloric acid and 400 ml of water were further added thereto, and when the solution was cooled, crystals were precipitated therefrom. The crystals were filtrated and recrystallized with 500 ml of water, and thus, Compound No. 5 was prepared. (Melting point: 267°-268° C.)

Synthesis Example-4 (Compund No. 8)

N-guanidinothiourea hydrochloride of 128 g were dissolved in 400 ml of aqueous 3N-NaOH solution and heat-reflux was applied for 3 hours.

After cooling, the reacted solution was neutralized with concentrated hydrochloric acid, and when cooled, crystals were precipitated therefrom and, the crystals were filtrated and were then recrystallized with 400 ml of water. Thus Compound No. 8 was obtained. (Melting point: 302°-304° C.)

The amount used of the compound having the aforegiven Formula[I] depends upon the kinds of a benzotriazole silver and a reducing agent to be used together, but is preferably between 0.001 mole and 10 moles thereof to 1 mole of a benzotriazole silver to be used and, more preferably, 0.005 to 0.5 moles thereof.

To the heat-developable image-pattern recording materials of the invention, a color toning agent may be applied with the purpose of blackening the image-patterns thereof.

As for the abovementioned color toning agents, the following compounds are given as the examples: the derivatives each of phthalimide, pyrazolone, quinazolinone, N-hydroxynaphthalimide, benzoxazine, naphthoxazinedione, 2,3-dihydro-phthalazinedione, 2,3-dihydro-1,3-oxazine-2,4-dione, oxypyridine, aminopyridine, hydroxyquinoline, aminoquinoline, isocarbostyryl, sulfonamide, 2H-1,3-benzothiazine-2,4-(3H)dione, benzotriazine, mercaptotriazole, dimercaptotetrazapentalene, phthalic acid, phthalazine, naphthalic acid, phthalamic acid, phthalazinone, and the like; the abovementioned compounds are described in the following patents: Japanese Patent O.P.I. Publication Nos. 4928/1971, 6077/1971, 5019/1974, 5020/1974, 91215/1974, 107727/1974, 2524/1975, 67132/1975, 67641/1975, 114217/1975, 33722/1977, 99813/1977, 1020/1978, 55115/1978, 76020/1978, 125014/1978, 156523/1979, 156524/1979, 156525/1979, 156526/1979, 4060/1980, 4061/1980, 32015/1980 and the like; W. German Pat. Nos. 2,140,406, 2,147,063, and 2,220,618; and U.S. Pat. Nos. 3,080,254, 3,847,612, 3,782,941, 3,994,732, 4,123,282, and 4,201,582; and the like.

In the heat-developable image-pattern recording materials of the invention, an additives having the following Formula [II] may be used with the purposes of accelerating developments, improving color-tones and the like:

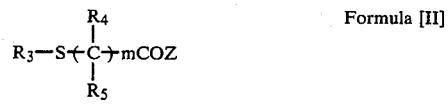

Formula [II]

wherein, $R_3$ represents an alkyl, aryl or heterocyclic radical which may have substituents; $R_4$ and $R_5$ may be the same with or the different from each other and represent hydroxy, or an alkyl aryl or heterocyclic radical which may respectively have the substituents therewith; Z represents a hydroxyl or amino radical; and m is an integer of 1 or 2.

In the abovegiven Formula [II], $R_3$ is preferably a substituted or unsubstituted alkyl radical having 1 to 7 carbon atoms, such as a methyl, ethyl, hydroxyethyl, carboxymethyl, carbamoylmethyl or benzyl radical and the like; a substituted or unsubstituted aryl radical, such as a phenyl, tryl, carboxyphenyl, carbamoylphenyl, hydroxyphenyl, or methylthiophenyl radical and the like; or a heterocyclic radical, such as a thienyl, benzothienyl, furyl, pyranyl, chromenyl, pyrrolyl, imidazolyl, pyridyl, pyrazyl, pyrimidinyl, indolidinyl, isothiazolyl, isoxazolyl, furazanyl, isochromenyl, pyrrolidinyl, 2-benzothiazolyl, 2-benzoimidazolyl, 1-phenyl-5-triazole, 2-thiadiazolyl and the like.

$R_4$ and $R_5$ are preferably hydrogen or a lower alkyl radical and, more preferably, hydrogen respectively.

The following are the concrete examples of the additives having Formula [II]:

| | |
|---|---|
| $C_2H_5SCH_2COOH$ | 1. |
| $HOCH_2CH_2SCH_2COOH$ | 2. |
| $HOCH_2CH_2SCHCOOH$<br>                          |<br>                          $CH_3$ | 3. |
| $HOCH_2CH_2SCH_2CONH_2$ | 4. |

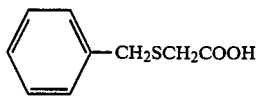

5.

-continued

6. 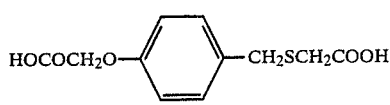

7. 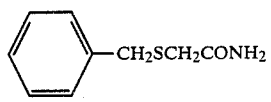

8. HOCOCH2SCH2COOH
9. NH2COCH2SCH2CONH2

10. 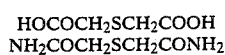

11. 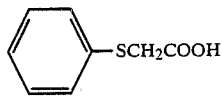

12. 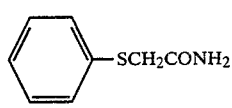

13. 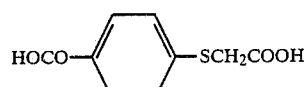

14. 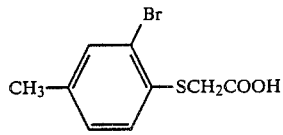

15. 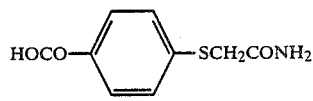

16. 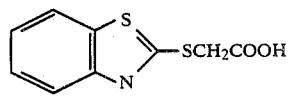

17. 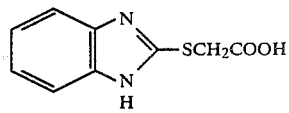

18. 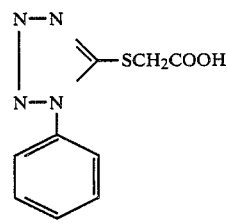

19. 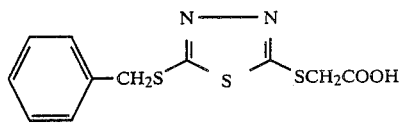

-continued

20. 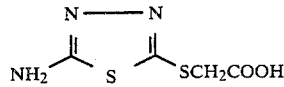

21. 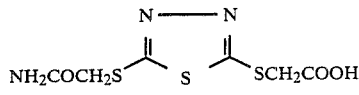

22. 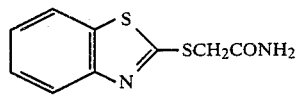

23. 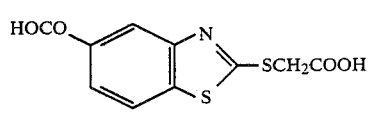

24. 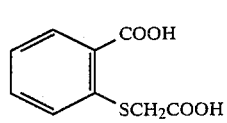

25. 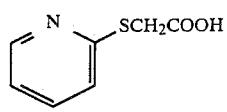

26. 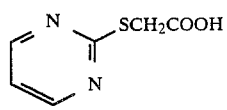

27. 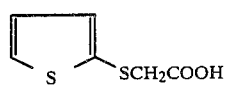

28. 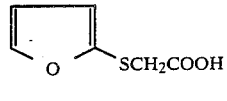

29. 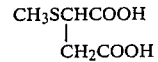

30. CH3SCH2CH2COOH
31. HOCH2CH2SCH2CH2COOH
32. HOCOCH2CH2SCH2CH2COOH

33. 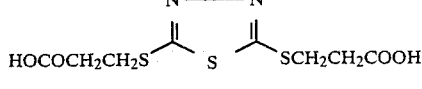

34. 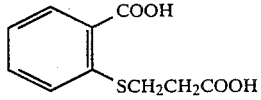

The amount of the additives having the abovegiven Formula [II] to be used depends upon the kinds of a benzotriazole silver, a reducing agent and the like, and is preferably between 0.001 and 10 moles to 1 mole of a benzotriazole silver and, more preferably, between 0.1 and 2 moles thereto.

For the purpose of preventing a heat-fogging on a heat developable image-pattern recording material of the invention, an antifoggant may be used. As for the antifoggants, the following examples thereof are given: a mercuric salt; an oxidizer such as an N-halogenacetamide, N-halogenosuccinimide, perchloric acid and the salts thereof, inorganic peroxide, persulfate, and the like; an acid and the salts thereof such as sulfinic acid, lauric acid, lithium, rosin, diterpenic acid, thiosulfonic acid and the like; a sulphur-containing compound such as a mercapto-compound-releasing compound, thiouracil, disulfide, simple sulphur, mercapto-1,2,4-triazole, thiazolinthione, polysulfide compound and the like; and besides, a compound of oxazoline, 1,2,4-triazole, phthalimide and the like; those compounds are respectively described in, for example, Japanese Patent Examined Publication No. 11113/1972, Japanese Patent O.P.I. Publication Nos. 90118/1974, 10724/1974, 97613/1974, 101019/1975, 130720/1974, 123331/1975, 47419/1976, 57435/1976, 78227/1976, 104338/1976, 19825/1978, 20923/1978, 50725/1976, 3223/1976, 42529/1976, 81124/1976, 51821/1979, 93149/1980 and the like; British Pat. No. 1,455,271; U.S. Pat. Nos. 3,885,968, 3,700,457, 4,137,079, and 4,138,265; W. German Pat. No. 2,617,907; and the like.

Heat-developable image-pattern recording material of the invention may also be allowed to contain a compound capable of releasing water through a heat treatment, that is the so-called water-releasing agents. As for such water-releasing agents, there may be given the examples, such as the compounds containing water of crystallization of sodium triphosphate dodecahydrate, sodium sulfate decahydrate, ammonium iron sulfate hexahydrate, ammonium alum tetracosahydrate, potassium alum tetracosahydrate, magnesium acetate tetrahydrate, manganese acetate tetrahydrate, or the like.

The heat-developable image-pattern recording materials of the invention may also be allowed to contain a compound having water-holding capacity for the purpose of maintaning the water contents of the image-pattern recording layer thereof at a certain degree. As for the compounds having such water-holding capacity, there may be given the examples such as polyalkyleneoxide, i.e., polyglycol, hydroxyethyl cellulose, carboxymethyl cellulose, and the like, as described in U.S. Pat. No. 3,347,675, for example.

Into the heat-developable image-pattern recording materials, it is possible to add, besides the abovementioned components, a variety of such a publicly known additive as a spectrosensitizing dye, antihalation agent, print-out preventing agent and the like, if necessary and arbitrarily.

As for the spectrosensitizing dyes, a cyanine, merocyanine, rhodacyanine styryl and the like, for example, which have a good effect on a silver halide emulsion, may be used.

As for the print-out preventing agents, there are given the examples thereof, such as tetrabromobutane, tribromethanol, 2-bromo-2-tolylacetamide, 2-bromo-2-tolylsulfonylacetamide, 2-tribromomethyl sulfonyl benzothiazole, 2,4-bis(tribromomethyl)-6-methyl triazine, and the like.

As for the supports to be used in the heat-developable image-pattern recording materials, there may be given the examples thereof, such as a synthetic plastic film, e.g., polyethylene film, cellulose acetate film, polyethylene terephthalate film and the like; a glass plate, a metal, and a paper-sheet, e.g., a base paper for photographic use, paper for printing use, baryta paper, resin-coated paper and the like. These supports may be allowed to have a subbing layers.

In the case that a heat-developable image-pattern recording material of the invention is to be used for an electrifying image-pattern recording material, it is desired that the support thereof is to be electro-conductive. As for such electroconductive supports, the examples thereof may be given such a matter comprising such a substrate material as a plastic film or a glass-plate coated thereon with an electroconductive layer, and such a matter as a metal plate having in itself an electroconductivity; and the like. Inter alia, paper or the like may be processed to embody into any type, and such a processed paper may therefore be used for the abovementioned supports. As for the methods for giving electroconductivity over to the surface of such a substrate material as a plastic film, a glass-plate or the like, there may be given such a method in which the surface of a substrate material is laminated, vacuum evaporated, applied a cathode spattering, an ionic plating or an electroless plating, or treated in the like manner to form an electroconductive coated layer.

Each of the components (a) to (d) to be used in a heat-developable image-pattern recording material of the invention is to form a heat-developable image-pattern recording layer in the manner that each of them is coated over to the support, together with a binder which was dissolved in water, an organic solvent or the mixture of water and an organic solvent.

The dried thickness of the image-pattern recording layer is 1 to 1,000$\mu$ and, more preferably, 3 to 20$\mu$. And, if necessary, an over-coat layer may be allowed to form on the abovementioned image-pattern recording layer. Each of the components (a) to (d) of the invention may be partly contained in the abovementioned support by the permeation or the like thereof from the heat-developable image-pattern recording layer. Each of the components (a) to (d) of the invention may also partly be contained in the abovementioned over-coat layer and/or subbing layer by the permeation or the like thereof from the heat-developable image-pattern recording layer.

In the case that a heat-developable image-pattern recording material of the invention thus prepared is a light-sensitive one, it is normally developed by heating it for 1 to 60 seconds in the range of the temperature of 80° C. to 200° C. after exposed to light. If necessary, it may be allowed to develop with bringing a water-impermeable material into close contact therewith. Also if further necessary, a preliminary heating may be applied thereto within the temperature range of 70° to 180° C. before the exposure thereof to light. As for the exposure light sources, the examples thereof may be given such as a glow lamp, tungsten lamp, fluorescent lamp, mercury lamp, iodine lamp, xenon lamp, LED light source, CRT light source, laser light source and the like.

In the case that a heat-developable image-pattern recording material of the invention is an electrifying recording material, the development thereof is made in the manner that a latent image-pattern is formed by electrifying imagewise in a suitable way and then heating is applied for 1 to 60 seconds within the temperature range of 80° C. to 200° C. Such development may be made in the course of the electrification. As for the electrifying means, there may be considered to use a variety of apparatuses for adjusting electric current. This type of the apparatuses includes a charged stencil or needle, a screen-adjustable or grid-adjustable discharger, or, a suitable photoconductive layer adjacent to an image-pattern recording layer. In the case that a photoconductor is used for adjusting electric current, it is possible to use a variety of exposure devices if a photoconductor is suitably selected. As for such an exposure means, there includes, for example, a tungsten lamp, xenon lamp, light emitting diode, laser beam, infrared ray and X-ray. As for the exposure light sources, any radiant ray sources may be used provided that the radiant ray generated by the exposure light source may induce a photoconductor.

The invention will be more concretely described in reference to the embodiments as follows. It is however to be understood stood that the invention and the embodiments thereof shall not be limited to the following examples.

EXAMPLE 1

Solution was prepared by dissolving 18.0 g (0.11 mole) of 5-nitrobenzotriazole into 300 ml of ethanol and whereto a solution prepared by dissolving 16.9 g (0.10 mole) of silver nitrate into 100 ml of water was dropped and the mixture thereof was stirred for 30 minutes. The crystals thus produced were filtrated and were then washed with 100 ml of ethanol, and thus, 26.4 g of 5-nitrobenzotriazole silver were obtained.

Thus obtained 5-nitrobenzotriazole silver of 13.5 g were added by 200 ml of ethanol and 250 ml of an aqueous solution of 8% polyvinyl butylal (i.e; Slec W-201, prepared by Sekisui Chemical Co.), and the mixture obtained was dispersed by a ball-mill for 24 hours, and thus, a dispersed solution was prepared.

Next, with stirring the dispersed solution, the following component chemicals were added successively thereinto to prepare a coating solution;

| (Component-1) | |
|---|---|
| Ascorbic acid in the form of 20% aqueous solution | 38 ml |
| (Component-2) | |
| Phthalic acid in the form of 10% methanol solution | 40 ml |
| (Component-3) | |
| Phthalazine in the form of 20% methanol solution | 15 ml |
| (Component-4) | |
| 4-ethyl-3-amino-5-mercapto-1,2,4-triazole (Compound-2) in the form of 2% methanol solution | 8 ml |

The coating solution thus prepared was coated over to a transparent electroconductive film (mfd. by Teijin; Electrodegrade; Surface resistivity: 500 Ω/cm$^2$) so that the silver amount may be 0.90 g per m$^2$, and thus Image-pattern recording material 1 was prepared.

Also, Image-pattern recording material 2 was prepared in quite the same manner to the abovementioned process, except that 9 ml of 2% methanol solution of 4-allyl-3-amino-5-mercapto-1,2,4-triazole (Compound-3) in place of the abovementioned Component-4. Similarly, Image-pattern recording material 3 was prepared by making use of 10 ml of 2% methanol solution of 4-phenyl-3-amino-5-mercapto-1,2,4-triazole (Compound 5). Also, similarly, Image-pattern recording material 4 was prepared by making use of 12 ml of 2% methanol solution of 4-phenyl-3-anilino-5-mercapto-1,2,4-triazole (Compound 13).

Further, for the purpose of controlling, Image-pattern recording material 5 was prepared by making use of 9 ml of 2% methanol solution of 4-allyl-3-mercapto-1,2,4-triazole in place of the abovementioned Components 4.

Still further, Image-pattern recording material 6 was prepared in quite the same manner as those mentioned above, except that nothing was added thereto for Component 4.

Each of the Image-pattern recording materials 1 to 6 thus prepared was brought into close contact with an electrode having a copper plate of 1 cm×1 cm in size on an insulating plate and the copper plate was maintained at +100 V to the electroconductive layer of the respective image-pattern recording materials, and electrification was applied for one second. After electrified, the image-pattern recording materials were separated from the copper plates, respectively.

Next, the voltage of the respective copper plates were neutralizing to zero to the electroconductive layers of the image-pattern recording materials, and then the same operations were repeated, respectively.

Then, each of the image-pattern recording materials was heated on a heating platen at 140° C. for 10 seconds and was developed.

The results thereof were that an image-pattern came out on the electrified areas of the image-pattern recording material whereto the voltage of +100 V was applied, and that no image-pattern came out on the image-pattern recording materials to which voltage was neutralized to zero.

The respective optical transmission density were as follows:

TABLE 1

| Sample No. | Compound Added | Density at 0 V | Density at 100 V |
|---|---|---|---|
| 1 | Compound 2 | 0.03 | 0.89 |
| 2 | Compound 3 | 0.03 | 0.86 |
| 3 | Compound 5 | 0.02 | 0.92 |
| 4 | Compound 13 | 0.03 | 0.77 |
| 5 | 4-allyl-3-mercapto-1,2,4-triazole | 0.03 | 0.06 |
| 6 | Nil | 0.04 | 0.08 |

Wherein, a density indicated is expressed in a relative value to the density value that is regarded as zero measured when the respective image-pattern recording materials were neither electrified nor heated.

EXAMPLE 2

A dispersion solution was prepared in the manner that 13.5 g of 5-nitrobenzotriazole silver were added by 200 ml of ethanol and 250 ml of 8% aqueous solution of polyvinyl butylal (mfd. by Sekisui Chemical Co., Slec W-201) and then by dispersing by means of a ball-mill for 24 hours. Next, with stirring the dispersion solution, the following component chemicals were added successively thereinto to prepare a coating solution.

| (Component-1) | |
|---|---|
| Silver iodide in the form of a cubic crystal emulsion having the average crystal size of 0.1 micron, containing 60 g of gelatin and 0.38 mole of silver per 1 kg of the emulsion | 13 ml |
| (Component-2) | |
| Sensitizing dye in the form of a 0.05 weight % of methanol solution of a merocyanine dye having the following formula | 3.8 ml |

-continued

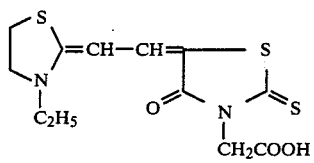

(Component-3)
| | |
|---|---|
| Ascorbic acid in the form of 20% aqueous solution | 38 ml |

(Component-4)
| | |
|---|---|
| Phthalic acid in the form of 10% methanol solution | 40 ml |

(Component-5)
| | |
|---|---|
| Phthalazine in the form of 20% methanol solution | 15 ml |

(Component-6)
| | |
|---|---|
| 4-ethyl-3-amino-5-mercapto-1,2,4-triazole (Compound-2) in the form of 2% methanol solution | 8 ml |

Image-pattern recording material 7 was prepared in the manner that the coating solution thus prepared was coated onto a photographic base paper so that the amount of silver may be 0.5 g per m².

Image-pattern recording material 8 was prepared in quite the same manner as that taken in the abovementioned preparation, except that 9 ml of 2% methanol solution of 4-allyl-3-amino-5-mecapto-1,2,4-triazole (Compound 3) were used in place of the abovementioned Component 6. Similarly, image-pattern recording material 9 was prepared by making use of 10 ml of 2% methanol solution of 4-phenyl-3-amino-5-mercapto-1,2,4-triazole (Compound 5). Also, similarly, Image-pattern recording material 10 was prepared by making use of 12 ml of 2% methanol solution of 4-phenyl-3-anilino-5-mercapto-1,2,4-triazole (Compound 13).

Further, for the purpose of controlling, Image-pattern recording material 11 was prepared by making use of 9 ml of 2% methanol solution of 4-allyl-3-mercapto-1,2,4-triazole, in place of the abovementioned Component 6.

Still further, Image-pattern recording material 12 was prepared in quite the same manner as those mentioned above except that nothing was added thereto for Component 6.

Each of the Image-pattern recording materials 7 to 12 was exposed to white light for 160 CMS (candela.-meter.second) through a step-wedge and was then heated to 120° C. for 10 seconds, and was thus developed. The results thus obtained are shown in Table 2.

For the purpose of testing the preservation stability of each sample 7 to 12, the respective image-pattern recording materials after developed were allowed to stand under a white fluorescent lamp of 1000 Lux to deteriorate and were then measured for the increase of the minimum density produced by printing-out. The results obtained are shown in the respective parentheses in the columns of minimum Density in the following Table 2.

TABLE 2

| Sample No. | Compound Added | Max. Density | Min. Density | (Deterioration Test) | Sensitivity (Note 1) |
|---|---|---|---|---|---|
| 7 | Compound 2 | 1.20 | 0.05 | (0.06) | 264 |
| 8 | Compound 3 | 1.28 | 0.05 | (0.07) | 282 |
| 9 | Compound 5 | 1.19 | 0.04 | (0.05) | 248 |

TABLE 2-continued

| Sample No. | Compound Added | Max. Density | Min. Density | (Deterioration Test) | Sensitivity (Note 1) |
|---|---|---|---|---|---|
| 10 | Compound 13 | 1.02 | 0.04 | (0.06) | 225 |
| 11 | 4-allyl-3-mercapto-1,2,4-triazole | 0.72 | 0.04 | (0.12) | 84 |
| 12 | Nil | 0.81 | 0.06 | (0.15) | 100 |

(Note 1)
Sensitivity is expressed in values relative to the sensitivity of Image-pattern recording material 12 for control use whose value is regarded as 100.

As is obvious from the table, the samples of the invention are proved to be excellent in the maximum density and sensitivity, and also in the prevention stability.

EXAMPLE 3

A dispersion solution was prepared in the manner that 13.5 g of 5-nitrobenzotriazole silver were added by 420 ml of ethanol and 20 g of polyvinyl butylal (Slec BL-1, mfd. by Sekisui Chemical Co.) and the mixture obtained was dispersed by means of a ball-mill for 24 hours. Next, with stirring the dispersion solution, the following component chemicals were added thereto successively to prepare a coating solution;

(Component-1)
| | |
|---|---|
| Silver iodide emulsion in form of a cubic crystal emulsion having the average crystal size of 0.03 microns, containing 20 g of polyvinyl butylal and 0.38 mole of silver per kg. of the emulsion. | 13 ml |

(Component-2)
| | |
|---|---|
| Sensitizing dye in form of a 0.05 weight % of methanol solution of a merocyanine dye having the following formula | 3.8 ml |

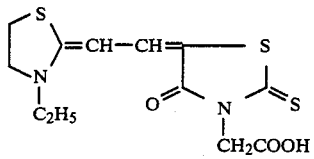

(Component-3)
| | |
|---|---|
| Ascorbic acid monopalmitate in the form of 20% ethanol solution | 50 ml |

(Component-4)
| | |
|---|---|
| Phthalic acid in form of 10% methanol solution | 40 ml |

(Component-5)
| | |
|---|---|
| Phthalazine in form of 20% methanol solution | 15 ml |

(Component-6)
| | |
|---|---|
| 4-ethyl-3-amino-5-mercapto-1,2,4-triazole (Compound-2) in the form of 2% methanol solution | 8 ml |

Image-pattern recording material 13 was prepared in the manner that the coating solution thus prepared was coated onto a photographic base paper so that the amount of silver may be 0.45 g per m².

Image-pattern recording material 14 was prepared in quite the same manner as that taken in the abovementioned preparation, except that 9 ml of 2% methanol solution of 4-allyl-3-amino-5-mercapto-1,2,4,-triazole (Compound 3) were used in place of the abovementioned Component 6. Similarly, Image-pattern recording material 15 was prepared by making use of 10 ml of 2% methanol solution of 4-phenyl-3-amino-5-mercapto-1,2,4-triazole (Compound 5). Also, similarly, Image-pattern recording material 16 was prepared by making use of 12 ml of 2% methanol solution of 4-phenyl-3-anilino-5-mercapto-1,2,4-triazole (Compound 13).

Further, for the purpose of controlling, Image-pattern recording material 17 was prepared by making use of 9 ml of 2% methanol solution of 4-allyl-3-mercapto-1,2,4-triazole, in place of the abovementioned Component 6.

Still further, Image-pattern recording material 18 was prepared in quite the same manner as those mentioned above, except that nothing was added thereto for Component 6.

Each of the image-pattern recording materials 13 to 18 was exposed to white light for 160 CMS (candela.-meter.second) through a step-wedge and was then heated to 120° C. for 10 seconds, and was thus developed. The results thus obtained are shown in Table 3:

TABLE 3

| Sample No. | Compound Added | Max. Density | Min. Density | Sensitivity (Note 2) |
|---|---|---|---|---|
| 13 | Compound 2 | 1.29 | 0.05 | 387 |
| 14 | Compound 3 | 1.30 | 0.04 | 406 |
| 15 | Compound 5 | 1.26 | 0.04 | 372 |
| 16 | Compound 13 | 1.19 | 0.04 | 298 |
| 17 | 4-allyl-3-mercapto-1,2,4-triazole | 0.25 | 0.04 | 62 |
| 18 | Nil | 0.30 | 0.05 | 100 |

(Note 2)
Sensitivity is expressed in values relative to the sensitivity of Image-pattern recording material 18 for control use whose value is regarded as 100.

EXAMPLE 4

A dispersion solution was prepared in the manner that 11.4 g of benzotriazole silver was added by 200 ml of ethanol and 250 ml of aqueous solution of 8% polyvinyl butylal (Slec W-201, mfd. by Sekisui Chemical Co.), and the mixture obtained was dispersed by means of a ball-mill for 24 hours. Next, with stirring the dispersion solution, the following component chemicals were added thereto successively to prepare a coating solution:

| (Component-1) | |
|---|---|
| Silver bromide emulsion, in form of a cubic crystal emulsion having the average crystal size of 0.1 micron containing 60 g of gelatin and 0.38 mole of silver per kg. of the gelatin | 13 ml |
| (Component-2) | |
| Sensitizing dye in form of a 0.05 weight % of methanol solution of a merocyanine dye having the following formula. | 3.8 ml |

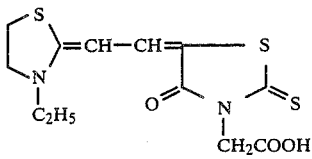

| (Component-3) | |
|---|---|
| Ascorbic acid in the form of 20% aqueous solution | 38 ml |
| (Component-4) | |
| Phthalic acid in form of 10% methanol solution | 40 ml |

| (Component-5) | |
|---|---|
| Phthalazine in form of 20% methanol solution | 15 ml |

Image-pattern recording material 19 was prepared in the manner that the coating solution thus prepared was coated onto a photographic base paper so that the amount of silver may be 0.5 g per m².

Image-pattern recording material 20 was prepared in quite the same manner so that taken in the abovementioned preparation, except that 9 ml of 2% methanol solution of 4allyl-3-amino-5-mercapto-1,2,4-triazole (Compound 3) were used in place of the abovementioned Component 6. Similarly, Image-pattern recording material 21 was prepared by making use of 10 ml of 2% methanol solution of 4-phenyl-3-amino-5-mercapto-1,2,4-triazole (Compound 5). Also, similarly, Image-pattern recording material 22 was prepared by making use of 12 ml of 2% methanol solution of 4-phenyl-3-anilino-5-mercapto-1,2,4-triazole (Compound 13).

Further, for the purpose of controlling, image-pattern recording material 23 was prepared by making use of 9 ml of 2% methanol solution of 4-allyl-3-mercapto-1,2,4-triazole, in place of the abovementioned Component 6.

Still further, Image-pattern recording material 24 was prepared in quite the same manner as those mentioned above, except that nothing was added thereto for Component 6.

Each of the Image-pattern recording materials 19 to 24 was exposed to white light for 160 CMS (candela.-meter.second) through a step-wedge and was then heated to 120° C. for 10 seconds, and was thus developed. The results obtained therefrom are shown in Table 4:

TABLE 4

| Sample No. | Compound Added | Max. Density | Min. Density | Sensitivity (Note 3) |
|---|---|---|---|---|
| 19 | Compound 2 | 1.49 | 0.05 | 295 |
| 20 | Compound 3 | 1.42 | 0.05 | 278 |
| 21 | Compound 5 | 1.38 | 0.04 | 264 |
| 22 | Compound 13 | 1.27 | 0.04 | 204 |
| 23 | 4-allyl-3-mercapto-1,2,4-triazole | 0.72 | 0.04 | 82 |
| 24 | Nil | 0.91 | 0.06 | 100 |

(Note 3)
Sensitivity is expressed in values relative to the sensitivity of Image-pattern recording material 24 for control use whose value is regarded as 100.

EXAMPLE 5

A dispersion solution was prepared in the manner that 11.4 g of benzotriazole silver were added by 420 ml of ethanol and 20 g of polyvinyl butylal (Slec BL-1, mfd. by Sekisui Chemical Co.) and the mixture obtained was dispersed by means of a ball-mill for 24 hours. Next, with stirring the dispersion solution, the following component chemicals were added thereto successively to prepare a coating solution:

| (Component-1) | |
|---|---|
| Silver iodide emulsion, in form of a cubic crystal emulsion having the average crystal size of 0.03 microns, containing 20 g of polyvinyl butylal and 0.38 mole of silver per kg of the emulsion | 13 ml |
| (Component-2) | |

| | | |
|---|---|---|
| Sensitizing dye in form of a 0.05 weight % of methanol solution of a merocyanine dye having the following formula | | 3.8 ml |

[Structure: merocyanine dye with S, =CH—CH, N-C₂H₅, O, N-CH₂COOH, S, S]

| | | |
|---|---|---|
| (Component-3) | | |
| Ascorbic acid monopalmitate in the form of 20% ethanol solution | | 50 ml |
| (Component-4) | | |
| Phthalic acid in form of 10% methanol solution | | 40 ml |
| (Component-5) | | |
| Phthalazine in form of 20% methanol solution | | 15 ml |
| (Component-6) | | |
| 4-ethyl-3-amino-5-mercapto-1,2,4-triazole (Compound-2) in the form of 2% methanol solution | | 8 ml |

Image-pattern recording material 25 was prepared in the manner that the coating solution thus prepared was coated onto a photographic base paper so that the amount of silver may be 0.45 g per m².

Image-pattern recording material 26 was prepared in quite the same manner as that taken in the abovementioned preparation, except that 9 ml of 2% methanol solution of 4-allyl-3-amino-5-mercapto-1,2,4-triazole (Compound 3) were used in place of the abovementioned Component 6. Similarly, Image-pattern recording material 27 was prepared by making use of 10 ml of 2% methanol solution of 4-phenyl-3-amino-5-mercapto-1,2,4-triazole (Compound 5). Also, similarly, Image-pattern recording material 28 was prepared by making use of 12 ml of 2% methanol solution of 4-phenyl-3-anilino-5-mercapto-1,2,4-triazole (Compound 13).

Further, for the purpose of controlling, Image-pattern recording material 29 was prepared by making use of 9 ml of 2% methanol solution of 4-allyl-3-mercapto-1,2,4-triazole, in place of the abovementioned Component 6.

Still further, Image-pattern recording material 30 was prepared in quite the same manner as those mentioned above, except that nothing was added thereto for Component 6.

Each of the image-pattern recording materials 25 to 30 was exposed to white light for 160 CMS (candela.-meter.second) through a step-wedge and was then heated to 120° C. for 10 seconds, and was thus developed. The results obtained therefrom are shown in Table 5:

TABLE 5

| Sample No. | Compound Added | Max. Density | Min. Density | Sensitivity (Note 4) |
|---|---|---|---|---|
| 25 | Compound 2 | 1.32 | 0.05 | 387 |
| 26 | Compound 3 | 1.40 | 0.06 | 362 |
| 27 | Compound 5 | 1.30 | 0.05 | 370 |
| 28 | Compound 13 | 1.27 | 0.04 | 325 |
| 29 | 4-allyl-3-mercapto-1,2,4-triazole | 0.37 | 0.04 | 89 |

TABLE 5-continued

| Sample No. | Compound Added | Max. Density | Min. Density | Sensitivity (Note 4) |
|---|---|---|---|---|
| 30 | Nil | 0.48 | 0.06 | 100 |

(Note 4)
Sensitivity is expressed in values relative to the sensitivity of Image-pattern recording material 30 for control use whose value is regarded as 100.

As are obvious from the tables 1 to 5, it can be understood that, in any case of Examples 1 to 5 the samples relating to the invention are relatively higher in the maximum density, and in Examples 2 to 5, the sensitivity thereof is higher as well, in comparison with the control-samples.

We claim:

1. A heat-developable image-pattern recording material of enhanced developability and stability having on a support a heat-developable image-pattern recording layer containing
   (a) a silver salt of a benzotriazole,
   (b) a reducing agent,
   (c) a binder and
   (d) at least one compound having the following Formula:

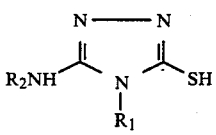

Formula [I]

wherein $R_1$ represents a hydrogen, an amino radical, or a substituted or unsubstituted alkyl, alkenyl or aryl radical; $R_2$ represents a hydrogen, an amino, alkyl, alkenyl or aryl radical.

2. A heat-developable image-pattern recording material according to claim 1 wherein an amount used in the layer of (a) is 0.5–50 mg of silver converted per dm², of (b) is 0.05–10 moles per mole of silver salt of benzotriazole and of (c) is 0.001–10 moles per mole of silver salt of benzotriazole.

3. A heat developable image-pattern recording material according to claim 1 wherein the material heat-developable image-pattern recording material contains a light-sensitive silver salt.

4. A heat-developable image-pattern recording material according to claim 1 wherein the material contains a compound of Formula:

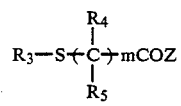

Formula [II]

wherein $R_3$ represents a substituted or unsubstituted alkyl, aryl or heterocyclic radical; $R_4$ and $R_5$ each represents a hydroxy or a substituted or unsubstituted alkyl, aryl or heterocyclic radical; Z represents a hydroxy or an amino radical; and m is an integer of 1 or 2.

5. A heat-developable image-pattern recording material according to claim 4 wherein contains an amount of the compound of Formula used in the layer is ranging from 0.001–10 moles per 1 mole of silver salt of benzotriazole.

6. A heat-developable image-pattern recording material according to claim 2 wherein said layer contains a light sensitive silver salt.

7. A heat-developable image-pattern material according to claim 1 wherein said layer contains a compound of Formula:

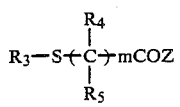  Formula [II]

wherein $R_3$ represents the substituted or unsubstituted alkyl, aryl or heterocyclic radical; $R_4$ and $R_5$ each represents a hydroxy or a substituted or unsubstituted alkyl, aryl or heterocyclic radical; Z represents a hydroxy or an amino radical; and m is an integer of 1 or 2.

8. A heat-developable image-pattern recording material according to claim 7 wherein said layer contains an amount of the compound of Formula ranging from 0.001–10 moles per 1 mole of silver salt of benzotriazole.

* * * * *